(12) United States Patent
Chung et al.

(10) Patent No.: US 10,640,756 B2
(45) Date of Patent: May 5, 2020

(54) METHOD OF PRODUCING MONOMERIC CARD IN BACTERIA

(71) Applicant: KOREA INSTITUTE OF SCIENCE AND TECHNOLOGY, Seoul (KR)

(72) Inventors: Hak Suk Chung, Seoul (KR); Jinsu An, Seoul (KR); Eun Gyeong Yang, Seoul (KR); So Yeon Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/244,361

(22) Filed: Jan. 10, 2019

(65) Prior Publication Data
US 2019/0338265 A1    Nov. 7, 2019

(30) Foreign Application Priority Data

May 2, 2018    (KR) .................. 10-2018-0050681

(51) Int. Cl.
*C12N 9/50*    (2006.01)
*C12N 15/70*    (2006.01)

(52) U.S. Cl.
CPC ............... *C12N 9/50* (2013.01); *C12N 15/70* (2013.01); *C12Y 304/22057* (2013.01); *C12Y 304/22064* (2013.01)

(58) Field of Classification Search
None
See application file for complete search history.

(56) References Cited

U.S. PATENT DOCUMENTS

2002/0176853 A1    11/2002    Reed et al.

OTHER PUBLICATIONS

Choi, "SerpinB1-mediated Modulation of Inflammatory Caspases," University of Southern California (dissertation), May 2017, 121 pages total.

*Primary Examiner* — Brian Gangle
(74) *Attorney, Agent, or Firm* — Birch, Stewart, Kolasch & Birch, LLP

(57) ABSTRACT

Provided is a method of producing monomeric caspase activation and recruitment domains (CARDs) in bacteria. According to this method, CARD domains may be easily produced in a monomeric form. Monomeric CARDs may be applied to studies on the mechanism of action of caspase, the development of new drugs, detection and elimination of endotoxins, development of cosmetics, etc.

16 Claims, 12 Drawing Sheets
Specification includes a Sequence Listing.

PROCASPASE (zymogen)

CARD DOMAIN

SEQUENCE LISTING

```
<160> NUMBER OF SEQ ID NOS: 16

<210> SEQ ID NO 1
<211> LENGTH: 377
<212> TYPE: PRT
<213> ORGANISM: Homo sapiens
<220> FEATURE:
<221> NAME/KEY: PEPTIDE
<222> LOCATION: (1)..(377)
<223> OTHER INFORMATION: Human caspase-4 protein

<400> SEQUENCE: 1

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Lys Tyr Tyr Asp Ala
        35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
65                  70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
            100                 105                 110

Glu Phe Leu Arg Leu Cys Lys Glu Arg Ala Glu Glu Ile Tyr Pro Ile
        115                 120                 125

Lys Glu Arg Asn Asn Arg Thr Arg Leu Ala Leu Ile Ile Cys Asn Thr
    130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175
```

```
Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
            195                 200                 205

Ser His Gly Ile Leu Glu Gly Ile Cys Gly Thr Val His Asp Glu Lys
210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Val Gln
                245                 250                 255

Ala Cys Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu
            275                 280                 285

Asp Ala Val Tyr Lys Thr His Val Glu Lys Asp Phe Ile Ala Phe Cys
            290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
            355                 360                 365

Arg Tyr Phe Tyr Leu Phe Pro Gly Asn
            370                 375

<210> SEQ ID NO 2
<211> LENGTH: 1131
<212> TYPE: DNA
<213> ORGANISM: Artificial Sequence
<220> FEATURE:
<223> OTHER INFORMATION: Polynucleotide encoding human caspase-4 protein

<400> SEQUENCE: 2 atggaggggta atcatcggaa aaaccgctg aaggtgctcg aatcactggg caaagacttt      60
cttactggtg tgctggataa cttggtcgaa caaaacgttc tgaactgaa agaagaagag     120 aaaaaaaaat actatgatgc aaaaacggaa gacaaggttc gcgtaatggc ggattcaatg     180
caggagaaac aacggatggc tggtcagatg cttctgcaga ccttttttcaa tattgatcag     240 attagcccaa caagaaagc gcatccgaac atggaggccg gtcctccgga gagcggagaa     300
agtaccgatg ctctgaagtt atgtccacac gaagagttc tgcgtctttg taaagaacgg     360
gctgaggaga tttatcccat caaagagcgt aataatcgta cacgtctggc gctgattatc     420
tgcaatacag aatttgatca tctgccgccg cgcaatggtg ccgacttcga tatcacgggg     480
atgaaggaac tgctggaagg tttagattac tccgttgacg tagaggaaaa tcttaccgcc     540
cgcgatatgg aaagtgcttt gcgtgcgttc gcaacccggc ccgaacacaa agttcggat      600 agtactttcc tggtgctcat gtcccacggg attctggaag gcatctgcgg tacggtccat     660
gacgaaaaga aacctgatgt tcttctgtat gacaccatct ttcaaatctt taacaaccgc     720
aactgtttat ccctgaaaga taaacccaag gtgatcattg tccaggcttg tcgggggggca     780 aaccgcggcg agctgtgggt gcgtgactct cctgcaagtc tcgaagttgc ttcaagccaa     840
tcatcggaaa acctggagga agacgcagtc tataaaactc atgttgagaa ggattttatc     900
```

```
gcgttctgct ctagtacacc tcataatgtg tcttggcgcg actcgaccat ggggtcaatc      960
ttcattacgc aactgatcac ctgttttcag aagtacagct ggtgttgcca tctcgaagaa     1020
gttttccgca aagtgcaaca gtcatttgag actccgcgtg ccaaagcgca aatgccgacc     1080
atcgaacgcc tctcgatgac acggtatttc tatcttttc cgggtaattg a               1131
```

```
<210> SEQ ID NO 3
<211> LENGTH: 31
<212> TYPE: DNA
<213> ORGANISM: Artificial Sequence
<220> FEATURE:
<223> OTHER INFORMATION: Forward primer for amplifying caspase-4
      polynucleotide

<400> SEQUENCE: 3
aggtcgtcat atggctgagg gtaatcattc g                                      31
```

```
<210> SEQ ID NO 4
<211> LENGTH: 39
<212> TYPE: DNA
<213> ORGANISM: Artificial Sequence
<220> FEATURE:
<223> OTHER INFORMATION: Reverse primer for amplifying caspase-4
      polynucleotide

<400> SEQUENCE: 4
ccgcaagctt tcaattaccc ggaaaaagat agaaatacc                              39
```

```
<210> SEQ ID NO 5
<211> LENGTH: 29
<212> TYPE: DNA
<213> ORGANISM: Artificial Sequence
<220> FEATURE:
<223> OTHER INFORMATION: Forward primer for amplifying caspase-4(C258A)
      polynucleotide

<400> SEQUENCE: 5
tcattgtcca ggctgctcgg ggggcaaac                                         29
```

```
<210> SEQ ID NO 6
<211> LENGTH: 29
<212> TYPE: DNA
<213> ORGANISM: Artificial Sequence
<220> FEATURE:
<223> OTHER INFORMATION: Reverse primer for amplifying caspase-4(C258A)
      polynucleotide

<400> SEQUENCE: 6
gtttgccccc cgagcagcct ggacaatga                                         29
```

```
<210> SEQ ID NO 7
<211> LENGTH: 377
<212> TYPE: PRT
<213> ORGANISM: Artificial Sequence
<220> FEATURE:
<223> OTHER INFORMATION: Caspase-4(C258A) protein

<400> SEQUENCE: 7
```

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Lys Tyr Tyr Asp Ala
        35                  40                  45

Lys Thr Glu Asp Lys Val Arg Val Met Ala Asp Ser Met Gln Glu Lys
 50                  55                  60

Gln Arg Met Ala Gly Gln Met Leu Leu Gln Thr Phe Phe Asn Ile Asp
 65                  70                  75                  80

Gln Ile Ser Pro Asn Lys Lys Ala His Pro Asn Met Glu Ala Gly Pro
                 85                  90                  95

Pro Glu Ser Gly Glu Ser Thr Asp Ala Leu Lys Leu Cys Pro His Glu
                100                 105                 110

Glu Phe Leu Arg Leu Cys Lys Glu Arg Ala Glu Glu Ile Tyr Pro Ile
                115                 120                 125

Lys Glu Arg Asn Asn Arg Thr Arg Leu Ala Leu Ile Ile Cys Asn Thr
130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
                180                 185                 190

Thr Arg Pro Glu His Lys Ser Ser Asp Ser Thr Phe Leu Val Leu Met
                195                 200                 205

Ser His Gly Ile Leu Glu Gly Ile Cys Gly Thr Val His Asp Glu Lys
210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Ala Arg Gly Ala Asn Arg Gly Glu Leu Trp Val Arg Asp Ser Pro
                260                 265                 270

Ala Ser Leu Glu Val Ala Ser Ser Gln Ser Ser Glu Asn Leu Glu Glu
                275                 280                 285

Asp Ala Val Tyr Lys Thr His Val Glu Lys Asp Phe Ile Ala Phe Cys
                290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
                340                 345                 350

Pro Arg Ala Lys Ala Gln Met Pro Thr Ile Glu Arg Leu Ser Met Thr
                355                 360                 365

Arg Tyr Phe Tyr Leu Phe Pro Gly Asn
                370                 375

<210> SEQ ID NO 8
<211> LENGTH: 1134
<212> TYPE: DNA
<213> ORGANISM: Artificial Sequence
<220> FEATURE:
<223> OTHER INFORMATION: Polynucleotide encoding caspase-4(C258A)
    protein

<400> SEQUENCE: 8
atggctgagg gtaatcatcg gaaaaaaccg ctgaaggtgc tcgaatcact gggcaaagac      60
tttcttactg gtgtgctgga taacttggtc gaacaaaacg ttctgaactg gaaagaagaa     120

```
gagaaaaaaa aatactatga tgcaaaaacg aagacaagg ttcgcgtaat ggcggattca    180
atgcaggaga acaacggat ggctggtcag atgcttctgc agacctttt caatattgat    240 cagattagcc caaacaagaa agcgcatccg aacatggagg ccggtcctcc ggagagcgga    300
gaaagtaccg atgctctgaa gttatgtcca cacgaagagt ttctgcgtct ttgtaaagaa    360
cgggctgagg agatttatcc catcaaagag cgtaataatc gtacacgtct ggcgctgatt    420
atctgcaata cagaatttga tcatctgccg ccgcgcaatg tgccgactt cgatatcacg    480 gggatgaagg aactgctgga aggtttagat tactccgttg acgtagagga aaatcttacc    540
gcccgcgata tggaaagtgc tttgcgtgcg ttcgcaaccc ggcccgaaca caaaagttcg    600
gatagtactt tcctggtgct catgtcccac gggattctgg aaggcatctg cggtacggtc    660
catgacgaaa agaaacctga tgttcttctg tatgacacca tctttcaaat ctttaacaac    720
cgcaactgtt tatccctgaa agataaaccc aaggtgatca ttgtccaggc tgctcggggg    780
gcaaaccgcg cgcgagctgtg ggtgcgtgac tctcctgcaa gtctcgaagt tgcttcaagc    840
caatcatcgg aaaacctgga ggaagacgca gtctataaaa ctcatgttga aaggattttt    900
atcgcgttct gctctagtac acctcataat gtgtcttggc gcgactcgac catgggtca    960 atcttcatta cgcaactgat cacctgtttt cagaagtaca gctggtgttg ccatctcgaa   1020
gaagttttcc gcaaagtgca acagtcattt gagactccgc gtgccaaagc gcaaatgccg   1080
accatcgaac gcctctcgat gacacggtat ttctatcttt ttccgggtaa ttga           1134

<210> SEQ ID NO 9
<211> LENGTH: 80
<212> TYPE: PRT
<213> ORGANISM: Artificial Sequence
<220> FEATURE:
<223> OTHER INFORMATION: Caspase-4 CARD polypeptide

<400> SEQUENCE: 9

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Lys Tyr Tyr Asp Ala
        35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
65                  70                  75                  80

<210> SEQ ID NO 10
<211> LENGTH: 243
<212> TYPE: DNA
<213> ORGANISM: Artificial Sequence
<220> FEATURE:
<223> OTHER INFORMATION: Polynucleotide encoding caspase-4 CARD
      polypeptide

<400> SEQUENCE: 10
atggctgagg gtaatcatcg gaaaaaaccg ctgaaggtgc tcgaatcact gggcaaagac     60
tttcttactg gtgtgctgga taacttggtc gaacaaaacg ttctgaactg gaaagaagaa   120
gagaaaaaaa aatactatga tgcaaaaacg aagacaagg ttcgcgtaat ggcggattca   180
atgcaggaga acaacggat ggctggtcag atgcttctgc agacctttt caatattgat   240 tga                                                                  243
```

<210> SEQ ID NO 11
<211> LENGTH: 45
<212> TYPE: DNA
<213> ORGANISM: Artificial Sequence
<220> FEATURE:
<223> OTHER INFORMATION: Forward primer for amplifying caspase-4 CARD
      polynucleotide

<400> SEQUENCE: 11
tctgcagacc tttttcaata ttgattgaaa gcttgcggcc gcact            45

<210> SEQ ID NO 12
<211> LENGTH: 45
<212> TYPE: DNA
<213> ORGANISM: Artificial Sequence
<220> FEATURE:
<223> OTHER INFORMATION: Reverse primer for amplifying caspase-4 CARD
      polynucleotide

<400> SEQUENCE: 12
agtgcggccg caagctttca atcaatattg aaaaaggtct gcaga            45

<210> SEQ ID NO 13
<211> LENGTH: 80
<212> TYPE: PRT
<213> ORGANISM: Artificial Sequence
<220> FEATURE:
<223> OTHER INFORMATION: Caspase-11 CARD polypeptide

<400> SEQUENCE: 13

Met Ala Glu Asn Lys His Pro Asp Lys Pro Leu Lys Val Leu Glu Gln
1               5                   10                  15

Leu Gly Lys Glu Val Leu Thr Glu Tyr Leu Glu Lys Leu Val Gln Ser
            20                  25                  30

Asn Val Leu Lys Leu Lys Glu Glu Asp Lys Gln Lys Phe Asn Asn Ala
        35                  40                  45

Glu Arg Ser Asp Lys Arg Trp Val Phe Val Asp Ala Met Lys Lys Lys
    50                  55                  60

His Ser Lys Val Gly Glu Met Leu Leu Gln Thr Phe Phe Ser Val Asp
65                  70                  75                  80

<210> SEQ ID NO 14
<211> LENGTH: 243
<212> TYPE: DNA
<213> ORGANISM: Artificial Sequence
<220> FEATURE:
<223> OTHER INFORMATION: Polynucleotide encoding caspase-11 CARD
      polypeptide

<400> SEQUENCE: 14
atggccgaaa acaagcaccc cgacaaaccc ctgaaagtat tggaacaact gggaaaggaa    60
gttctgacgg agtaccttga aaaattagtc caatccaatg ttttaaagct gaaagaggaa   120
gacaaacaga gtttaacaa cgctgagcgc tctgacaaac gctgggtttt cgtcgatgcg   180
atgaagaaaa acattcaaa ggtcggcgag atgctgcttc agacttttt ttccgttgat   240 tga                                                                243

<210> SEQ ID NO 15
<211> LENGTH: 28
<212> TYPE: DNA
<213> ORGANISM: Artificial Sequence
<220> FEATURE:

```
<223> OTHER INFORMATION: Forward primer for amplifying caspase-11 CARD
      polynucleotide

<400> SEQUENCE: 15
aggtcgtcat atggccgaaa acaagcac                                          28

<210> SEQ ID NO 16
<211> LENGTH: 39
<212> TYPE: DNA
<213> ORGANISM: Artificial Sequence
<220> FEATURE:
<223> OTHER INFORMATION: Reverse primer for amplifying caspase-11 CARD
      polynucleotide

<400> SEQUENCE: 16
agcgtactcg agtcaatcaa cggaaaaaaa agtctgaag                              39
```

METHOD OF PRODUCING MONOMERIC CARD IN BACTERIA

CROSS-REFERENCE TO RELATED APPLICATION

This application claims the benefit of Korean Patent Application No. 10-2018-0050681, filed on May 2, 2018, in the Korean Intellectual Property Office, the entire disclosure of which is hereby incorporated by reference.

BACKGROUND

1. Field

The present disclosure relates to a method of producing monomeric CARD domains in bacteria.

2. Description of the Related Art

Caspases are cysteine-aspartic proteases or cysteine-dependent aspartate-directed proteases, and are proteases that play essential roles in apoptosis, necrosis, and inflammation. The failure of apoptosis is one of the main causes of tumorigenesis and autoimmune diseases, and unwanted apoptosis may cause local ischemia or Alzheimer's disease.

Caspase consists of a prodomain, a large subunit, and a small subunit and is expressed as an inactive procaspase in cells. When cell death signals are delivered to cells, the inactive procaspase is cleaved into three domains by autolysis to remove the prodomain. Two large subunits each of 21-17 kDa and two small subunits each of 10-12 kDa associate to form an active caspase.

Caspase activation and recruitment domains (CARDs) are interaction motifs found in a wide array of proteins, and mainly involved in processes relating to inflammation and apoptosis. CARD domains mediate the formation of larger protein complexes via direct interactions between individual CARD domains. For example, in an intrinsic apoptotic pathway, caspases are recruited via CARD-CARD interactions, and this leads to the formation of a caspase activating multiprotein complex called the apoptosome. Initiator caspase-9 and executioner caspases are activated to cause apoptosis. It is known that a CARD domain recognizes lipopolysaccharides, which are endotoxins, as a main cause of sepsis to activate caspase-4, caspase-5, or caspase-11, leading to pyroptosis via formation of inflammasome and non-canonical inflammasome, which causes septic shock or sepsis.

Accordingly, it is necessary to develop a method of easily producing monomeric CARD domains for the development of new drugs, prevention of sepsis, detection and elimination of endotoxins, and the like.

SUMMARY

Provided is a method of producing monomeric caspase activation and recruitment domains (CARDs) in bacteria.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
FIG. 1 is a schematic diagram illustrating a structure of a caspase domain and a caspase activation and recruitment domain (CARD)
Figure 1:
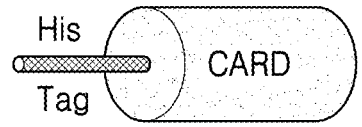

An aspect provides a method of producing monomeric caspase activation and recruitment domains (CARDs) in bacteria, the method including:

introducing a vector including a polynucleotide encoding a caspase (Casp) protein into bacteria to prepare transformed bacteria;

culturing the transformed bacteria to induce expression of caspase;

lysing the cultured bacteria to obtain a lysate; and obtaining monomeric CARDs from the lysate.

The method may include introducing a vector including a polynucleotide encoding a caspase (Casp) protein into bacteria to prepare transformed bacteria.

The "caspase" is a cysteine-aspartic protease or cysteine-dependent aspartate-directed protease, and is a protease that plays roles in apoptosis, necrosis, and inflammation. The caspase consists of a prodomain, a large subunit, and a small subunit. The caspase may be expressed as an inactive procaspase in cells. The procaspase may form an active caspase by autolysis in cells. The active caspase may include a large subunit of about 21-17 kDa and a small subunit of about 10-12 kDa.

The caspase may be selected from the group consisting of caspase-1, caspase-2, caspase-4, caspase-5, caspase-9, caspase-11, caspase-12, and caspase-13. The caspase-4 is a protease that cleaves other proteins at aspartic acid residues. The caspase-4 is a human-derived protein, and a murine homolog to caspase-4 is caspase-11.

The caspase may be a wild-type caspase or a mutant caspase. The mutant caspase may have a substitution (C258A) of alanine (A) for cysteine (C) which is an amino acid at position 258 from the N-terminus thereof. The caspase may be a protein including an amino acid sequence selected from the group consisting of SEQ ID NOS: 1, 7, 9, and 13. The caspase may include an amino acid sequence encoded by a nucleotide sequence selected from the group consisting of SEQ ID NOS: 2, 8, 10, and 14.

The vector may be an expression vector. The expression vector may be an expression vector generally known to those skilled in the art. The expression vector may be, for example, a plasmid vector, a cosmid vector, and a bacteriophage vector. The expression vector may include a promoter for expression of a target protein, an antibiotic resistance gene, a selection marker, and an origin of replication. The expression vector may include a nucleotide sequence encoding an affinity tag.

The vector may include a polynucleotide encoding an affinity tag. The affinity tag may be a polyhistidine tag (e.g., 6×His), FLAG, glutathione-S-transferase (GST), maltose binding protein (MBP), NusA, thioredoxin, ubiquitin, BAP, STREP, chitin binding protein (CBP), chitin binding domain (CBD), hemagglutinin (HA), S-tag, Small Ubiquitin-like Modifier (SUMO) or a combination thereof.

The term "bacteria" may be prokaryotic bacteria. The bacteria may be bacteria of the genus *Escherichia*. The bacteria may be *Escherichia coli*. The *Escherichia coli* may be C41(DE3), CLEARCOLI BL21(DE3), CMR300, BL21 (DE3), BL21(DE3)pLysS, BL21-Gold(DE3), BL21-Gold (DE3)pLysS, ROSETTA™ (DE3), ROSETTA™ (DE3)pLysS, ROSETTA™ 2(DE3), ROSETTA™ 2(DE3)pLysS, ROSETTA™ 2(DE3)pLacI, ROSETTA™ (DE3)pLacI, C43 (DE3), W3110, MG1655, MC1000, BW25113, or DH5α. For example, the *Escherichia coli* may be a strain selected from the group consisting of C41(DE3), CLEARCOLI BL21(DE3), and CMR300.

The introducing may be transformation, transduction, or transfection. The introducing may be performed by, for example, calcium chloride or calcium phosphate coprecipitation, electroporation, a DEAE-dextran mediated method, or lipofection.

The term "transformed bacteria" refer to bacteria that are mutated to express a target protein by introducing a polynucleotide encoding the target protein into a host using a vector. The transformed bacteria may be live *Escherichia coli* and may express procaspase, caspase, or CARD monomers from a polynucleotide encoding the caspase.

The method may include culturing the transformed bacteria to induce expression of caspase.

The transformed bacteria may be those cultured in a medium containing an antibiotic. The antibiotic may be ampicillin, bleomycin, carbenicillin, chloramphenicol, coumermycin, gentamicin, kanamycin, spectinomycin, tetracycline or a combination thereof.

The culturing may be performed at a temperature of about 15° C. to about 40° C., about 15° C. to about 25° C., about 15° C. to about 20° C., about 15° C. to about 18° C., about 30° C. to about 40° C., about 30° C. to about 38° C., about 30° C. to about 36° C. The culturing may be performed for about 1 hr or more, 2 hrs or more, 5 hrs or more, 8 hrs or more, 12 hrs or more, or overnight. The culturing may be performed under shaking.

The method may include lysing the cultured bacteria to obtain a lysate. The lysing of the cultured bacteria may be performed by a physical or chemical method. The physical method may be performed by, for example, sonication, French Press or repeated freezing/thawing. The chemical method may be performed by, for example, a surfactant. The active caspase may be obtained by treating the obtained transformant with sonication, repeated freezing/thawing, addition of a surfactant, centrifugation, or a combination thereof.

The lysing of the cultured bacteria may be performed in the presence of a surfactant. The surfactant may be selected from the group consisting of TWEEN 20, TWEEN 80, TRITON X-100, TRITON X-114, NP-40, BRIJ-35, BRIJ-58, octyl glucoside, octyl thioglucoside, n-Dodecyl β-D-maltoside (DDM), 3-[(3-cholamidopropyl) dimethylammonio)-1-propanesulfonate (CHAPS), and 3-[(3-cholamidopropyl) dimethylammonio]-2-hydroxy-1-propanesulfonate (CHAPSO).

The lysing of the cultured bacteria may be performed by sonicating the bacteria.

The method may further include heat-treating the lysate. The heat-treating may be performed at a temperature of about 50° C. to about 80° C., about 55° C. to about 80° C., about 60° C. to about 80° C., about 65° C. to about 75° C., or about 65° C. to about 70° C. The heat-treating may be performed for about 1 min to about 3 hrs, about 5 min to about 2 hrs, about 10 min to about 1 hr, about 10 min to about 45 min, or about 20 min to about 30 min.

The method may include obtaining monomeric CARDs from the lysate.

The term "monomer or monomeric" refers to a low-molecular-weight substance which is a unit constituting a polymer compound, etc. The monomeric protein may be one of proteins forming a multiprotein complex. The monomeric CARD may be one CARD polypeptide that constitutes a multiprotein formed by binding via interaction of CARD and CARD proteins. The monomeric CARD may be a polypeptide including an amino acid sequence of SEQ ID NO: 9. The monomeric CARD may be a polypeptide including an amino acid sequence encoded by a nucleotide sequence of SEQ ID NO: 10.

The lysate may be subjected to a method selected from the group consisting of affinity chromatography, size-exclusion chromatography, ion-exchange chromatography, hydrophobic interaction chromatography, and high-performance liquid chromatography (HPLC). The affinity chromatography may be a nickel (Ni) affinity chromatography. The nickel affinity chromatography may be nickel-nitrilotriacetic acid (Ni-NTA) or nickel-iminodiacetic acid (Ni-IDA) affinity chromatography. The size-exclusion chromatography may include a gel selected from the group consisting of SUPERDEX, SUPEROSE, SEPHACRYL, SEPHADEX, PL GEL, cross-linked polyacrylamide, agarose gel, and Styragel.

A method according to an aspect may be used to easily produce monomeric caspase activation and recruitment domains (CARDs). The monomeric CARDs may be applied to studies on the mechanism of action of caspase, the development of new drugs, detection and elimination of endotoxin, development of cosmetics, etc.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, the present disclosure will be described in more detail with reference to Examples. However, these Examples are for illustrative purposes only, and the scope of the present disclosure is not intended to be limited by these Examples.

Example 1. Preparation of Vector Including Polynucleotide Encoding Caspase-4 (C258A), Caspase-4 CARD, or Caspase-11 CARD in *Escherichia coli*

1. Preparation of pET28b-His-Casp4 (C258A)

To obtain a polynucleotide (GenBank Accession No. A48861.1) encoding human caspase-4 polypeptide (SEQ ID NO: 1), a caspase-4 polynucleotide (SEQ ID NO: 2) codon-optimized for *Escherichia coli* was purchased from Integrated DNA Technologies (IDT, USA).

Polymerase chain reaction (PCR) was performed using a pair of the following primers to amplify a synthetic polynucleotide encoding the caspase (Casp)-4 polypeptide.

```
Caspase-4 forward primer:
                                       (SEQ ID NO: 3)
5'-AGGTCGTCATATGGCTGAGGGTAATCATTCG-3'

Caspase-4 reverse primer:
                                       (SEQ ID NO: 4)
5'-CCGCAAGCTTTCAATTACCCGGAAAAAGATAGAAATACC-3'
```

Throughout the experimental procedures, KOD hot start DNA polymerase (Novagen) was used for PCR in a T3000 thermocycler (Biometra).

The amplified product was purified using a DokDo-Prep PCR purification kit (ELPIS), and the purified product was introduced into a pET28b plasmid (Novagen). The cloned plasmid was transformed into chemically competent *Escherichia coli* DH5u by heat shock, and selected on an LB-kanamycin plate.

The cloned plasmid pET28b-His-Casp4 was prepared from the selected *Escherichia coli* using a Dokdo-Prep Plasmid DNA Mini-prep kit (ELPIS). To prepare an inactive mutant caspase-4 (C258A) using the prepared plasmid as a template, circular site directed mutagenesis PCR was performed using a pair of the following primers.

```
C258A forward primer:
                                       (SEQ ID NO: 5)
5'-TCATTGTCCAGGCTGCTCGGGGGGCAAAC-3'

C258A reverse primer:
                                       (SEQ ID NO: 6)
5'-GTTTGCCCCCCGAGCAGCCTGGACAATGA-3'
```

The amplified product was treated with restriction enzyme Dpn1 (Elpis) to remove the template plasmid. Nicked pET28b-His-Casp4(C258A) was transformed into *Escherichia coli* DH5α. pET28b including a nucleotide sequence (SEQ ID NO: 8) encoding caspase-4 (C258A) (SEQ ID NO: 7) was named pET28b-His-Casp4(C258A).

2. Preparation of pET28b-His-Casp4 CARD

A plasmid pET28b-His-Casp4 CARD expressing human caspase-4 Caspase activation and recruitment domain (CARD) was prepared.

In detail, circular site directed mutagenesis PCR was performed using the pET28b-His-Casp4 plasmid prepared as described in Example 1.1 as a template and a pair of the following primers to amplify a polynucleotide (SEQ ID NO: 10) encoding Casp4 CARD domain (SEQ ID NO: 9).

```
Casp4 CARD forward primer:
                                       (SEQ ID NO: 11)
5'-TCTGCAGACCTTTTTCAATATTGATTGAAAGCTTGCGGCCGCACT-3'

Casp4 CARD reverse primer:
                                       (SEQ ID NO: 12)
5'-AGTGCGGCCGCAAGCTTtcaATCAATATTGAAAA AGGTCTGCAGA-3'
```

The amplified product was treated with restriction enzyme Dpn1 (Elpis), and then transformed into *Escherichia coli*, followed by selection. The prepared plasmid was named pET28b-His-Casp4 CARD.

3. Preparation of pET28b-His-Casp11 CARD

To obtain a polynucleotide encoding a murine caspase-11 CARD polypeptide, a synthetic gene codon-optimized for *Escherichia coli* was purchased from Integrated DNA Technologies (IDT, USA). PCR was performed using a pair of the following primers to amplify a polynucleotide (SEQ ID NO: 14) encoding a caspase-11 CARD polypeptide (SEQ ID NO: 13).

```
Casp11 CARD forward primer:
                                       (SEQ ID NO: 15)
5'-AGGTCGTCATATGGCCGAAAACAAGCAC-3'

Casp11 CARD reverse primer:
                                       (SEQ ID NO: 16)
5'-AGCGTACTCGAGTCAATCAACGGAAAAAAAAGTCTGAAG-3'
```

As described in Example 1.1, PCR was performed and the amplified product was purified. The purified product was cloned into pET28b (Novagen). The cloned plasmid was transformed into *Escherichia coli*, followed by selection, as described in Example 1.1. The cloned plasmid was named pET28b-His-Casp11 CARD.

4. Preparation of pBAD33.1-His-Casp4(C258A)

An expression vector expressing human Caspase-4 (C258A) protein was prepared.

In detail, the pET28b-His-Casp4(C258A) plasmid described in Example 1.2 was treated with restriction enzymes XbaI (Elpis) and HindIII (Elpis). A caspase-4 (C258A) polynucleotide containing a ribosome binding site (RBS) and 6× histidine tag was isolated and purified using a QIAquick Gel Extraction Kit (QIAGEN, Germany). The purified product was cloned into pBAD33.1 (Chung, H. S., and Raetz, C. R., Biochemistry (2010), vol. 49(19), p. 4126-4137). The cloned plasmid was transformed into *Escherichia coli*, followed by selection, as described in Example 1.1. The cloned plasmid was named pBAD33.1-His-Casp4 (C258A).

5. Preparation of pBAD33.1-His-Casp4 CARD

To prepare a plasmid pBAD33.1-His-Casp4 CARD expressing human Caspase-4 CARD, the pET28b-His-Casp4 CARD plasmid was treated with restriction enzymes XbaI (Elpis) and HindIII (Elpis). A caspase-4 (C258A) polynucleotide containing RBS and 6× histidine tag was isolated and purified using a QIAquick Gel Extraction Kit (QIAGEN, Germany). The purified product was cloned into pBAD33.1. The cloned plasmid was transformed into *Escherichia coli*, followed by selection, as described in Example 1.1. The cloned plasmid was named pBAD33.1-His-Casp4 CARD.

Example 2. Isolation of Monomeric Inactive Caspase-4 from *Escherichia coli*

1. Expression of Monomeric Caspase-4 (C258A) in *Escherichia coli* Strain

The pET28b-His-Casp4(C258A) prepared as described in Example 1.1 was transformed into an *Escherichia coli* strain C41(DE3) (Dumon-Seiqnovert, L., Prot. Express. Purif., 2004, Vol. 37(1), p. 203-206) and CLEARCOLI BL21(DE3) (Lucigen). The pBAD33.1-His-Casp4(C258A) prepared as described in Example 1.4 was transformed into an *Escherichia coli* strain CMR300 (Reynolds, C. M., Biochemistry. 2009 Oct. 13; 48(40), p. 9627-9640). CLEARCOLI BL21 (DE3) and CMR300 which are the *Escherichia coli* strains have lipid $IV_A$, instead of lipopolysaccharide (LPS), in outer membrane.

Each of the transformed strains was cultured on a solid medium containing an appropriate antibiotic. Single colonies from the respective plates were seeded in 10 ml of LB medium containing the antibiotic, and cultured at about 30° C. overnight. 1:100 dilution of the culture cultured overnight was seeded in 1 L of LB medium containing the appropriate antibiotic, and cultured at about 30° C. When $OD_{600}$ reached about 0.4, the temperature was decreased to about 18° C. When $OD_{600}$ reached about 0.8, 0.2 mM isopropyl 3-D-1-thiogalactopyranoside (IPTG, UBPBio, USA) was added to the *Escherichia coli* strain transformed with pET28b-His-Casp4(C258A) about 18° C., and 0.1% (w/v) arabinose was added to the *Escherichia coli* strain transformed with pBAD33.1-His-Casp4(C258A).

Figure 2:
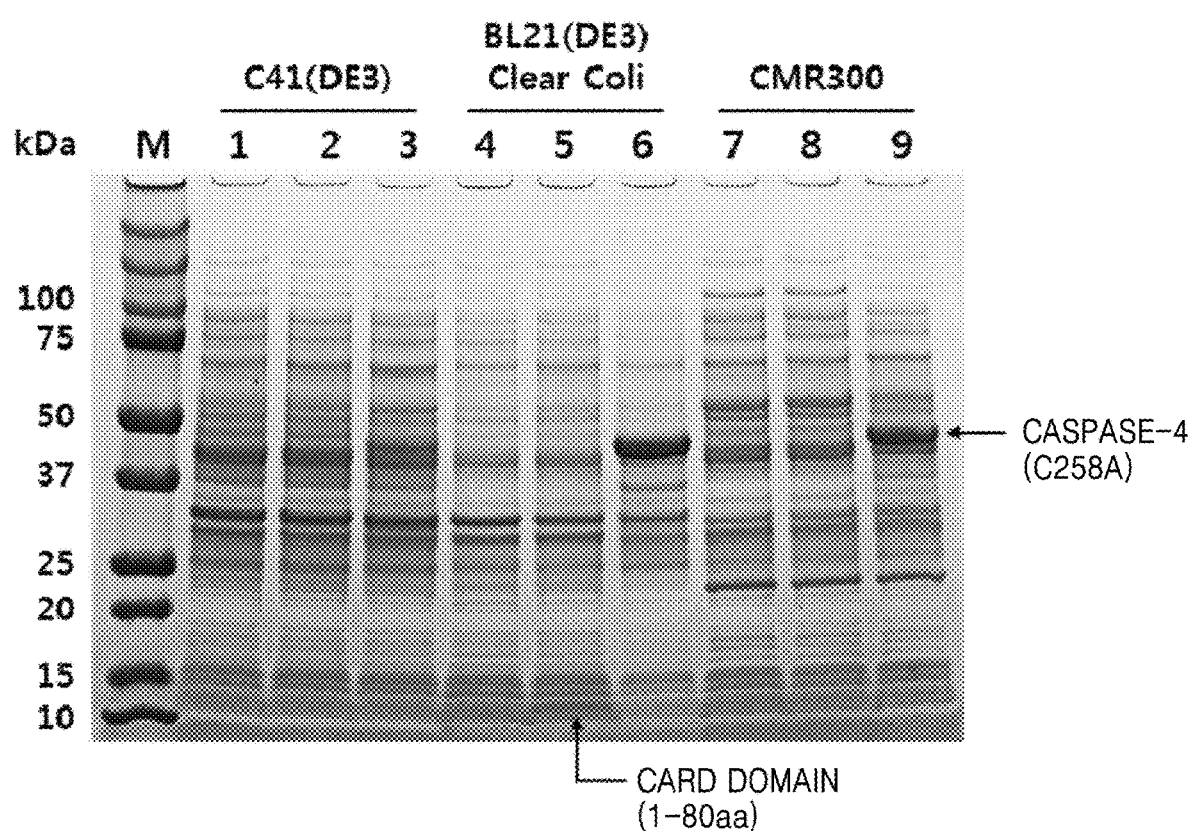
FIG. 2 shows SDS-PAGE results of comparing expression rates of caspase-4 (C258A) between *Escherichia coli* strains.

Thereafter, the each *Escherichia coli* strain was cultured at about 18° C. for about 16 hours to induce expression of caspase. Expression of inactive caspase-4 (C258A) was confirmed by SDS-PAGE. SDS-PAGE showing a comparison of expression rates of caspase-4 (C258A) between the *Escherichia coli* strains is shown in FIG. 2 (M: protein marker, lane 1: proteins of C41(DE3) cell line containing pET28b, lane 2: C41(DE3) cell containing pET28b-His-Casp4 CARD, lane 3: C41(DE3) cell containing pET28b-His-Casp4 (C258A), lane 4: CLEARCOLI BL21(DE3) cell containing pET28b, lane 5: CLEARCOLI BL21(DE3) cell containing pET28b-His-Casp4 CARD, lane 6: CLEARCOLI BL21(DE3) cell containing pET28b-His-Casp4(C258A), lane 7: CMR300 cell containing pBAD33.1, lane 8: CMR300 cell containing pBAD33.1-His-Casp4 CARD, lane 9: CMR300 cell containing pBAD33.1-His-Casp4(C258A)).

In FIG. 2, lanes 1, 4, and 7 indicate those transformed with a vector having no caspase-4-encoding gene; lanes 2, 5, and 8 indicate those transformed with a vector having caspase-4 CARD-encoding gene; and lanes 3, 6, and 9 indicate those transformed with a vector having inactive caspase-4 gene.

As shown in FIG. 2, higher expression of caspase-4 (C258A) was observed in CLEARCOLI BL21(DE3) and CMR300 which have lipid $IV_A$, instead of LPS, in outer membrane.

2. Purification of Monomeric Caspase-4 (C258A)

Figure 3:
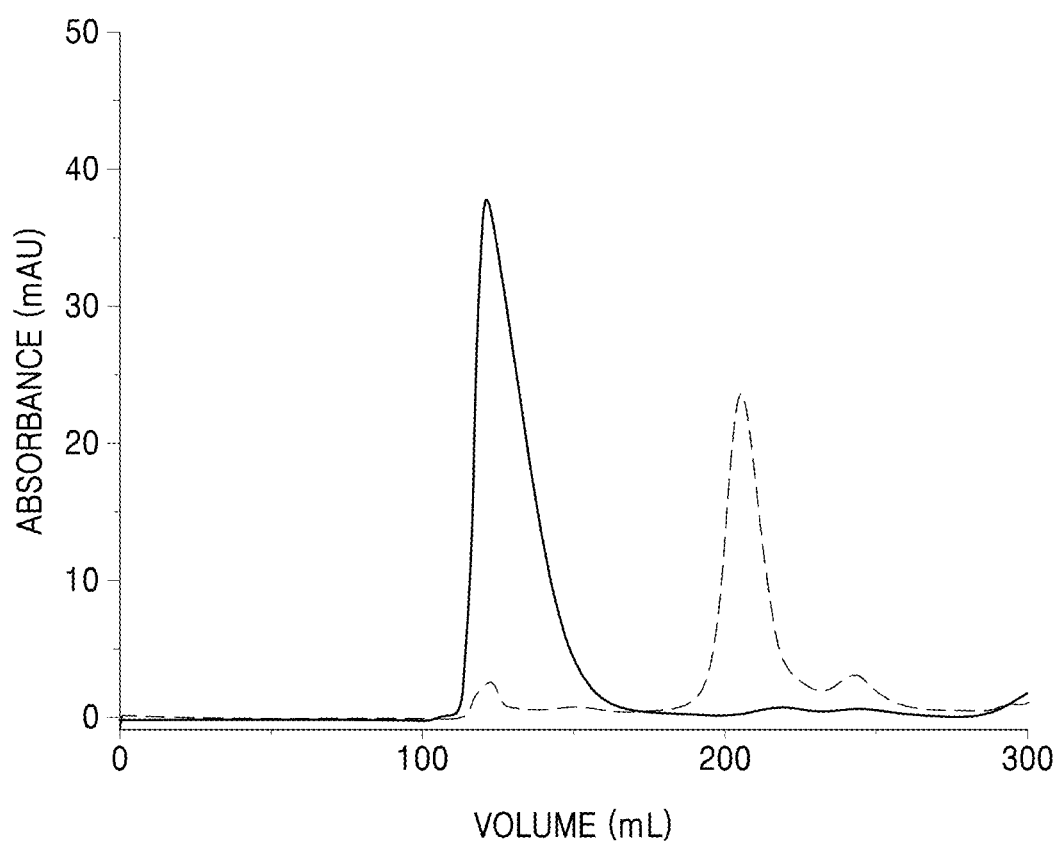
FIG. 3 is a graph showing results of size-exclusion chromatography of cell lysates according to treatment with TWEEN 20 during cell lysis (broken line: treatment with TWEEN 20, solid line: non-treatment with TWEEN 20)

Cells cultured as described in Example 2.1 were obtained, and the obtained cells were suspended in a buffer containing 20 mM Tris-HCl (pH 7.9) (Biosesnag, Korea), 300 mM NaCl, 20 mM imidazole (Bio basic, Canada), 5 mM beta-mercaptoethanol (BME), protease inhibitor cocktail (Sigma-Aldrich) with or without 1% (v/v) TWEEN 20 (Bio-Rad, USA). Difference according to treatment with TWEEN 20 during cell lysis was examined by size-exclusion chromatography, and the results are shown in FIG. 3 (broken line: treatment with TWEEN 20, solid line: non-treatment with TWEEN 20). As shown in FIG. 3, when TWEEN 20 was not treated during cell lysis, aggregated proteins were obtained. In contrast, when TWEEN 20 was added, monomeric proteins were obtained.

Figure 4A:
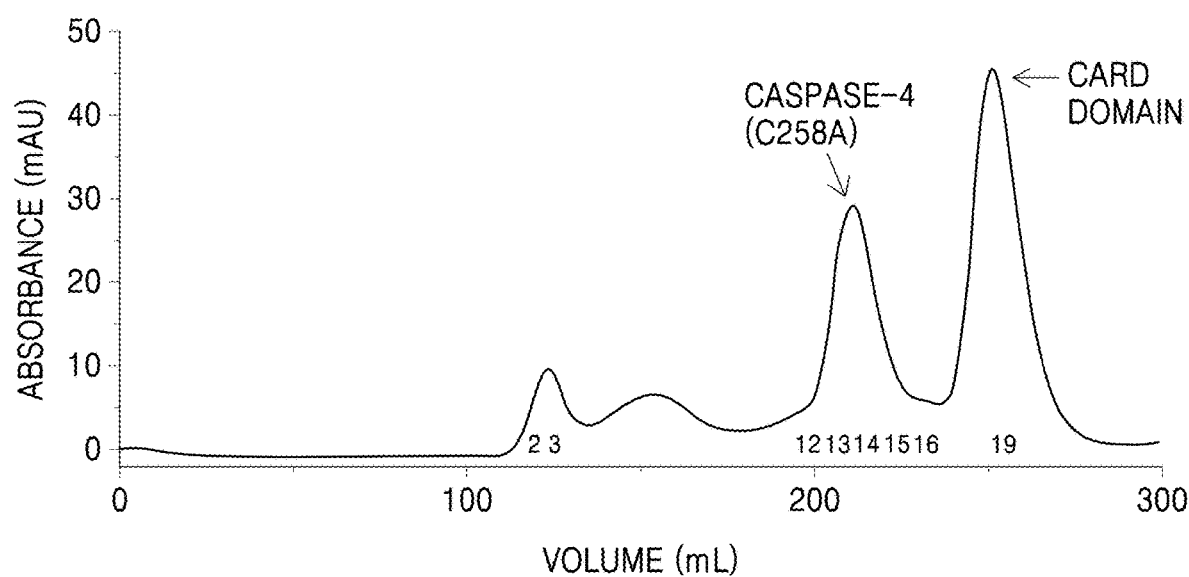
FIGS. 4A and 4B are a graph and an SDS-PAGE image showing results of size-exclusion chromatography of caspase-4 (C258A) and a CARD domain expressed in CLEARCOLI BL21(DE3), respectively.
Figure 4B:
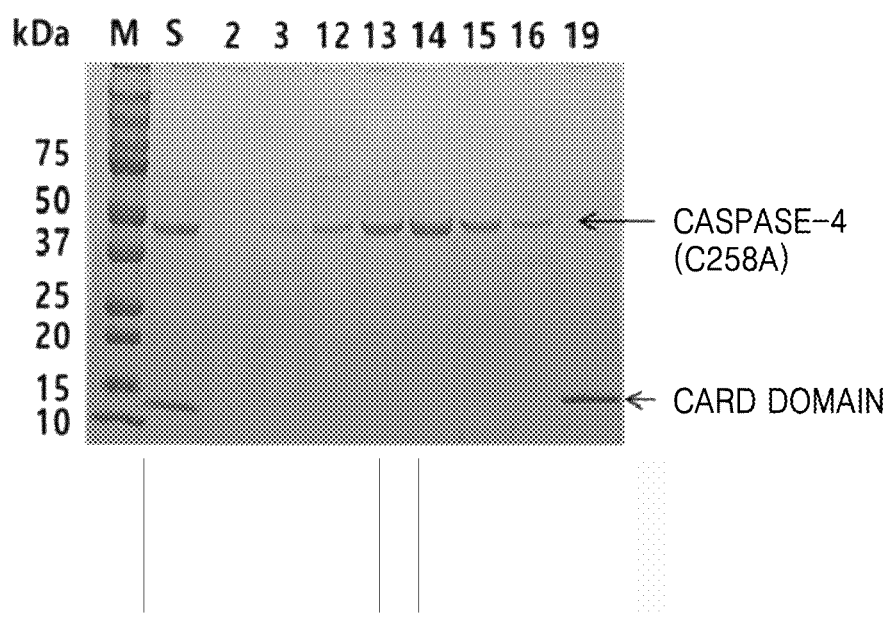
Figure 4C:
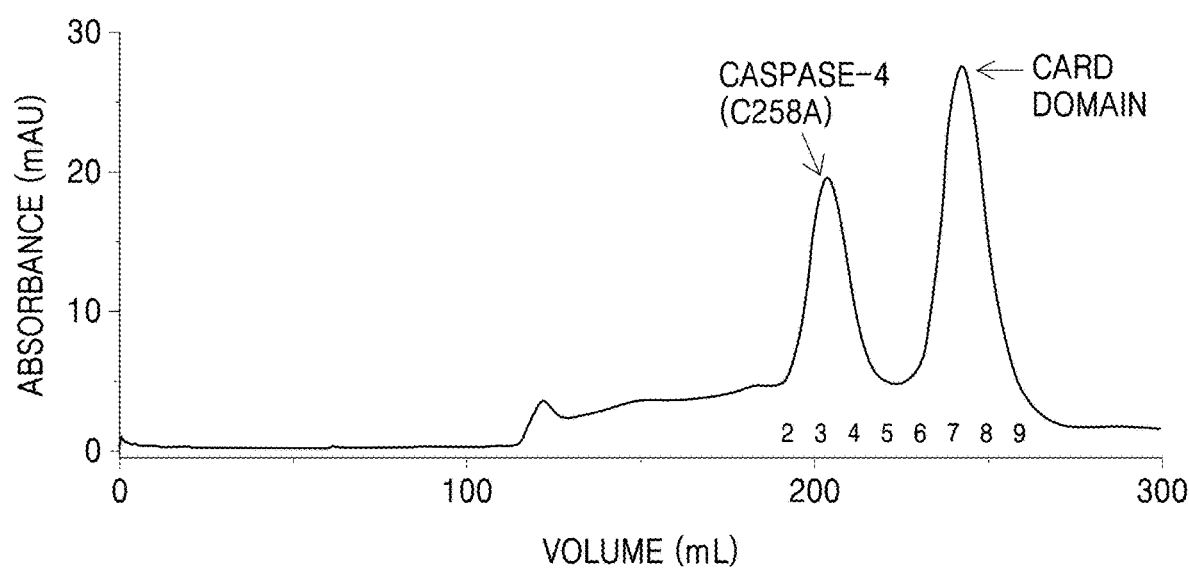
FIGS. 4C and 4D are a graph and an SDS-PAGE image showing results of size-exclusion chromatography of caspase-4 (C258A) and a CARD domain expressed in C41(DE3), respectively.
Figure 4D:
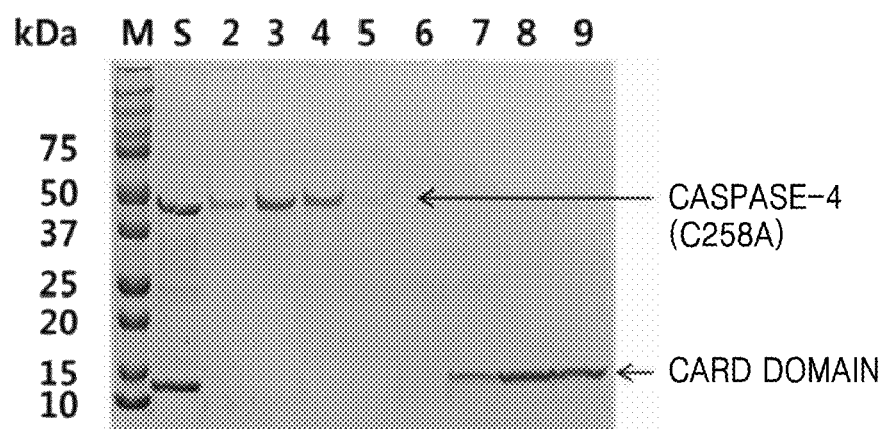

The suspended cells were lysed by sonication, and a lysate was centrifuged at a speed of 20,000×g for 30 minutes at 4° C. A supernatant was loaded on HisTrap HP (GE Healthcare Life Sciences) equilibrated with buffer A [20 mM Tris-HCl (pH 7.9), 300 mM NaCl, and 20 mM imidazole] in advance at 4° C. For Ni-NTA affinity chromatography, HisTrap HP column was washed with 50 column volumes of 43 mM imidazole, and proteins were eluted with a linear gradient of imidazole from 43 mM to 250 mM using an AKTApurifier UPC 100 system (GE Healthcare Life Sciences). Thereafter, the eluted proteins were loaded on HiLoad 26/600 SUPERDEX™ 200 pg column (GE Healthcard Life Sciences). Size-exclusion chromatography was carried out using the AKTApurifier UPC 100 system and buffer B [20 mM HEPES (pH 7.5) (Bio basic, Canada), 300 mM NaCl, 10% (v/v) glycerol (Sigma-Aldrich), 0.5 mM tris(2-carboxyethyl) phosphine (TCEP) (Hampton research, USA)], and proteins were examined by SDS-PAGE. Graphs and SDS-PAGE images showing the results of the size-exclusion chromatography are shown in FIGS. 4A to 4D. FIGS. 4A and 4B show results of purifying the proteins expressed in CLEARCOLI BL21 (DE3), and FIGS. 4C and 4D show results of purifying the proteins expressed in C41(DE3). In FIG. 4B, 'M' indicates a protein marker, lane 'S' indicates the protein purified by Ni-NTA, lanes 2 and 3 indicate the aggregated caspase-4 (C258A) isolated by size-exclusion chromatography, lanes 12 to 16 indicate the monomeric caspase-4 (C258A) isolated by size-exclusion chromatography, and lane 19 indicates the monomeric CARD domain isolated by size-exclusion chromatography. In FIG. 4D, 'M' indicates a protein marker, lane 'S' indicates the protein purified by Ni-NTA, lanes 2 to 5 indicate the monomeric caspase-4 (C258A) isolated by size-exclusion chromatography, and lanes 7 to 9 indicate the monomeric CARD domain isolated by size-exclusion chromatography.

As shown in FIGS. 4A to 4D, when procaspase-4 (C258A) (Zymogen) was purified from *Escherichia coli*, both of procaspase-4 (C258A) and CARDs cleaved by protease were obtained by size-exclusion chromatography. Therefore, this purification method may be used to obtain monomeric caspase-4 (C258A) in a zymogen form and monomeric CARD domains at the same time.

Concentrations of the proteins eluted at the respective purification procedures were determined using a Bradford protein assay kit II (Bio-Rad, USA), and determined yields of purified caspase-4 (C258A) per 1 L are shown in Table 1 (NA: not detected).

TABLE 1

| | Ni-NTA affinity chromatography | Size-exclusion chromatography |
|---|---|---|
| ClearColi BL21(DE3) | 6.4 mg/L | 4.0 mg/L |
| C41(DE3) | 5.25 mg/L | NA |

Figure 5A:
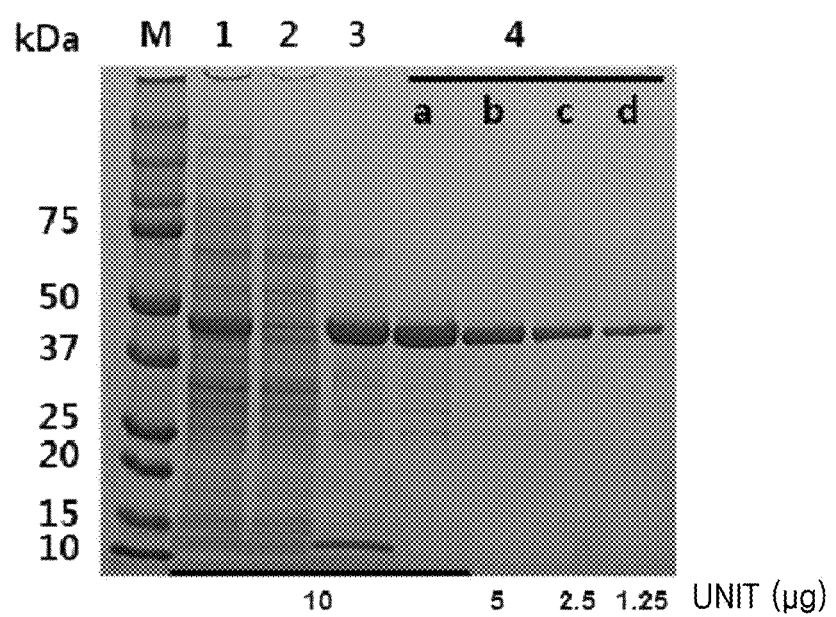
FIGS. 5A and 5B are an SDS-PAGE image and a graph showing results of size-exclusion chromatography of caspase-4 (C258A) expressed in CLEARCOLI BL21(DE3), respectively.
Figure 5B:
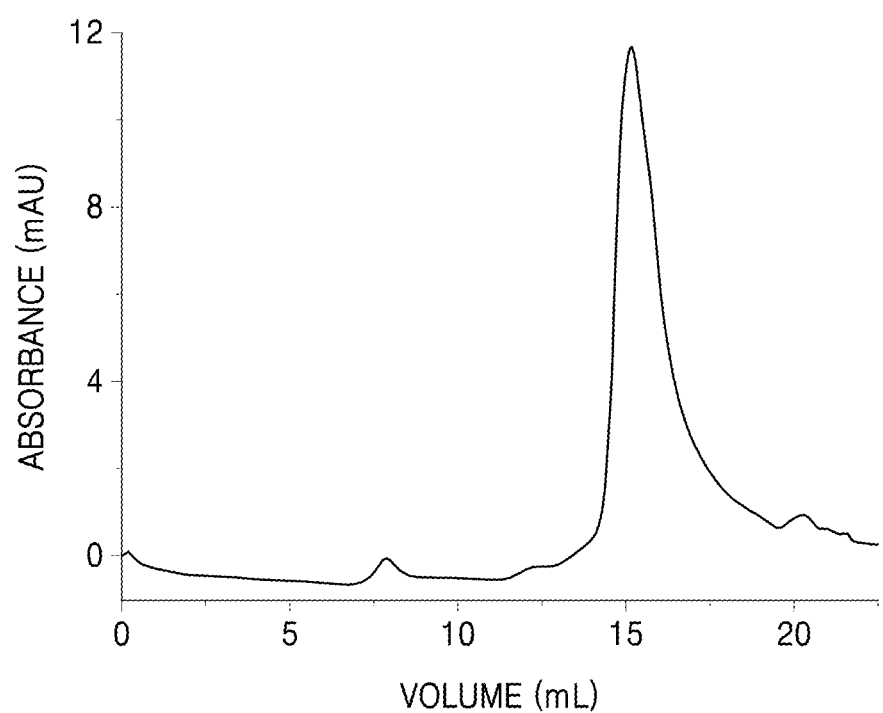

Further, purity of the purified caspase-4 (C258A) was confirmed by SDS-PAGE, and homogeneity of purified caspase-4 (C258A) was confirmed by size-exclusion chromatography. An SDS-PAGE image and a graph of size-exclusion chromatography are shown in FIGS. 5A and 5B, respectively (in FIG. 5A, M: protein marker, lane 1: cell lysate, lane 2: supernatant resulting from centrifugation, lane 3: Ni-NTA affinity chromatography, lanes 4a to 4d: caspase-4 (C258A) purified by size-exclusion chromatography, lane 4a: 10 μg of purified protein, lane 4b: 5 μg of purified protein, lane 4c: 2.5 μg of purified protein, lane 4d: 1.25 μg of purified protein).

As shown in FIGS. 5A and 5B, although the yield of caspase-4 (C258A) expressed in CLEARCOLI BL21(DE3) was slightly increased, it was confirmed that a surfactant such as 1% (v/v) TWEEN 20 is needed in a cell suspension for purification of monomeric caspase-4 (C258A), irrespective of the kind of *Escherichia coli*.

3. Identification of Monomeric Caspase-4 (C258A)

A molecular weight of the purified inactive caspase-4 (C258A) was more precisely measured by ultracentrifugation at the New Drug Development Center, Daegu Gyeongbuk Medical Innovation Foundation. A concentration of the protein sample used in the measurement was 1.7 mg/ml. ProteomeLab XL-A (Beckman Coulter) ultracentrifuge and AN 60 Ti rotor were used. Absorbance was measured at 280 nm at 20 min intervals at a rotor speed of 42,000 rpm and 20° C., and molecular weight calculations were performed using SEDFIT program. A theoretical molecular weight of the monomeric inactive caspase-4 and a measured molecular weight of the protein by ultracentrifugation are shown in Table 2 (three independent experiments, mean±standard deviation).

TABLE 2

| | Theoretical molecular weight | Measured molecular weight |
|---|---|---|
| His-Casp4(C258A) | 45.4 kDa | 42.4 ± 1.4 kDa |

As shown in Table 2, it was confirmed that the inactive caspase-4 purified from *Escherichia coli* strain by the purification procedure containing TWEEN 20 exists as a monomer.

Example 3. Expression of CARD Domain of Caspase-4 in *Escherichia coli* and Purification as Monomer 1. Expression of CARD Domain of Caspase-4 in *Escherichia coli* and Purification as Monomer The pET28b-His-Casp4 CARD prepared as described in Example 1.2 was transformed into *Escherichia coli* strains, C41(DE3) and CLEARCOLI BL21(DE3). Further, the pBAD33.1-His-Casp4 CARD domain prepared in Example 1.5 was transformed into *Escherichia coli* strain CMR300.

Each of the transformed strains was cultured on a solid medium containing an appropriate antibiotic. Single colonies from the respective plates were seeded in 10 ml of LB medium containing the antibiotic, and cultured at about 30° C. overnight. 1:100 dilution of the culture cultured overnight was seeded in 1 L of fresh LB medium containing the appropriate antibiotic, and cultured at about 30° C. When $OD_{600}$ reached about 0.4, the temperature was decreased to about 18° C. When $OD_{600}$ reached about 0.8, 0.2 mM IPTG was added to the *Escherichia coli* strain transformed with pET28b-His-Casp4 CARD at about 18° C., and 0.1% (w/v) arabinose was added to the *Escherichia coli* strain transformed with pBAD33.1-His-Casp4 CARD. Thereafter, each strain was cultured at about 18° C. for about 16 hrs to induce expression of CARD domain.

The cultured cells were harvested and the harvested cells were suspended in buffer A. The suspended cells were lysed by sonication, and a lysate was centrifuged at a speed of 20,000×g for about 30 min at about 4° C. Since CARD domain has heat resistance, solubility may be maintained even after heat treatment at about 70° C. for about 30 min. After heat treatment at about 70° C. for about 30 min, centrifugation was performed at a speed of 20,000×g for about 30 min at about 4° C. A supernatant was loaded on HisTrap HP equilibrated with buffer A in advance at about 4° C., and HisTrap HP column was washed with 10 column volumes of buffer A supplemented with 0.1% (v/v) TWEEN 20. Thereafter, the column was washed with 50 column volumes of 43 mM imidazole in buffer A, and proteins were eluted with a linear gradient of imidazole from 43 mM to 250 mM in buffer A using the AKTApurifier UPC 100 system. Thereafter, the eluted proteins were loaded on HiLoad 26/600 SUPERDEX™ 200 pg column, and size-exclusion chromatography was carried out using buffer C (20 mM HEPES (pH 7.5), 300 mM NaCl) and the AKTApurifier UPC 100 system. Concentrations of the proteins eluted at the respective purification procedures were determined using the Bradford protein assay kit II, and yields of purified caspase-4 CARD domain per 1 L were determined and shown in Table 3.

TABLE 3

| | Ni-NTA affinity chromatography | Size-exclusion chromatography |
|---|---|---|
| ClearColi BL21(DE3) | 6.0 mg/L | 5.3 mg/L |

Figure 6A:
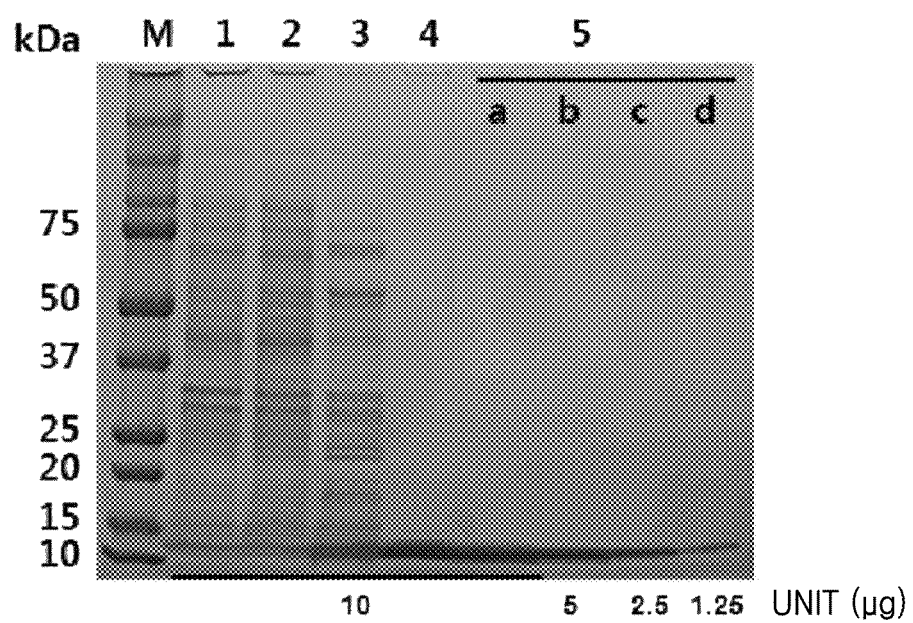
FIGS. 6A and 6B are an SDS-PAGE image and a graph showing results of size-exclusion chromatography of a caspase-4 CARD expressed in CLEARCOLI BL21(DE3), respectively.
Figure 6B:
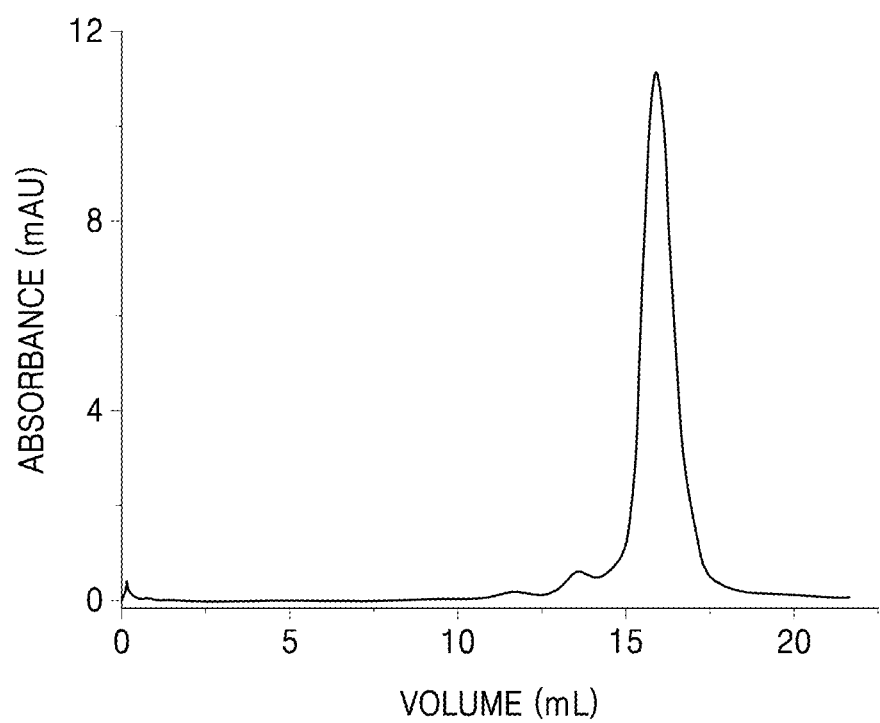

Further, purity of the purified caspase-4 CARD domain was confirmed by SDS-PAGE, and homogeneity of purified caspase-4 CARD domain was confirmed by size-exclusion chromatography. An SDS-PAGE image and a graph of size-exclusion chromatography are shown in FIGS. 6A and 6B, respectively (in FIG. 6A, M: protein marker, lane 1: cell lysate, lane 2: supernatant resulting from centrifugation, lane 3: supernatant after heat treatment, lane 4: Ni-NTA affinity chromatography, lane 5: size-exclusion chromatography, lane 5a: 10 μg of purified protein, lane 5b: 5 μg of purified protein, lane 5c: 2.5 μg of purified protein, lane 5d: 1.25 μg of purified protein As shown in FIGS. 6A and 6B, it was confirmed that expression of CARD domain was observed only in CLEARCOLI BL21(DE3) strain.

2. Identification of Monomeric Caspase-4 CARD

A theoretical molecular weight of monomeric CARD domain is 11.6 kDa, which is hard to be separated through the size-exclusion chromatography column used for the separation. Therefore, the molecular weight of the purified caspase-4 CARD domain was more precisely measured by ultracentrifugation at the New Drug Development Center, Daegu Gyeongbuk Medical Innovation Foundation. A protein sample having a concentration of 1.5 mg/ml was used to measure the molecular weight of caspase-4 CARD domain by the method described in Example 2.2. The result is shown in Table 4 in comparison with the theoretical molecular weight (three independent experiments, mean±standard deviation).

TABLE 4

| | Theoretical molecular weight of monomeric caspase-4 CARD domain | Measured molecular weight of monomeric caspase-4 CARD domain |
|---|---|---|
| His-Casp4 CARD domain | 11.6 kDa | 11.0 ± 0.3 kDa |

As shown in Table 4, it was confirmed that the purified CARD domain from *Escherichia coli* strain exists as a monomer.

Example 4. Expression of CARD Domain of Caspase-11 in *Escherichia coli* and Purification as Monomer The pET28b-His-Casp11 CARD prepared as described in Example 1.3 was transformed into CLEARCOLI BL21 (DE3) which is an *Escherichia coli* strain. The transformed strain was cultured on a solid medium containing an appropriate antibiotic. A single colony from the plate was seeded in 10 ml of LB medium containing the antibiotic, and cultured at about 30° C. overnight. 1:100 dilution of the culture cultured overnight was seeded in 1 L of fresh LB medium containing the appropriate antibiotic, and cultured at about 30° C. When $OD_{600}$ reached about 0.4, the temperature was decreased to about 18° C. When $OD_{600}$ reached about 0.8, 0.2 mM IPTG was added and cultured at about 18° C. for about 16 hrs to induce expression of CARD domain.

Figure 7:
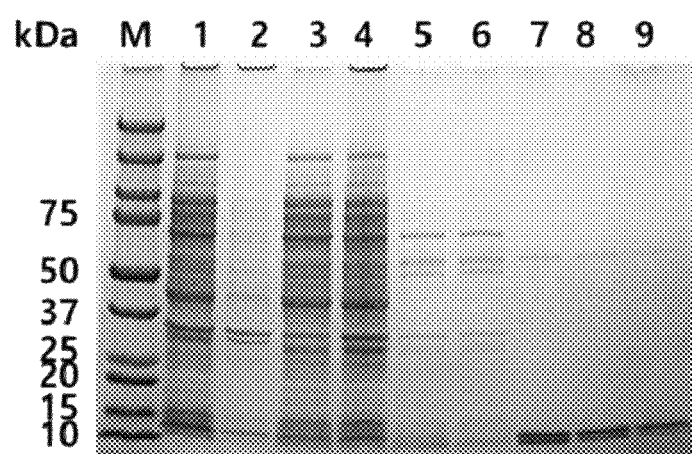
FIG. 7 is an SDS-PAGE image of a CARD domain of caspase-11 expressed in CLEARCOLI BL21(DE3).

The protein was purified as described in Example 3.1, and the purification procedure and purity of the purified protein were confirmed by SDS-PAGE, and an image thereof is shown in FIG. 7 (M: protein marker, lane 1: whole protein in cells, lane 2: insoluble protein after sonication, lane 3: soluble protein after sonication, lane 4: insoluble protein after heat treatment, lane 5: soluble protein after heat treatment, lane 6: flow through Ni-NTA column, lanes 7 to 9: caspase-11 CARD protein purified by Ni-NTA).

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of producing monomeric caspase activation and recruitment domains (CARDs) in bacteria, the method comprising:
introducing a vector comprising a polynucleotide encoding a caspase (Casp) protein into bacteria to prepare transformed bacteria;
culturing the transformed bacteria to induce expression of caspase;
lysing the cultured bacteria to obtain a lysate; and
obtaining monomeric CARDs from the lysate.

2. The method of claim 1, wherein the caspase is selected from the group consisting of caspase-1, caspase-2, caspase-4, caspase-5, caspase-9, caspase-1, caspase-12, and caspase-13.

3. The method of claim 1, wherein the caspase is a wild-type caspase or a mutant caspase.

4. The method of claim 3, wherein the mutant caspase has a substitution (C258A) of alanine (A) for cysteine (C) which is an amino acid at position 258 from the N-terminus thereof.

5. The method of claim 1, wherein the caspase is a protein comprising an amino acid sequence selected from the group consisting of SEQ ID NOS: 1, 7, 9, and 13.

6. The method of claim 1, wherein the vector comprises a polynucleotide encoding an affinity tag.

7. The method of claim 6, wherein the affinity tag is a polyhistidine tag, glutathione-S-transferase (GST), maltose binding protein (MBP), NusA, thioredoxin, ubiquitin, biotin acceptor peptide (BAP), chitin binding protein (CBP), chitin binding domain (CBD), hemagglutinin (HA), S-tag, Small Ubiquitin-like Modifier (SUMO), or a combination thereof.

8. The method of claim 1, wherein the bacteria are *Escherichia coli*.

9. The method of claim 8, wherein the *Escherichia coli* is selected from the group consisting of C41(DE3), BL21 (DE3), and CMR300.

10. The method of claim 1, wherein the bacteria are cultured in a medium comprising an antibiotic.

11. The method of claim 1, wherein the lysing of the cultured bacteria is performed in the presence of a surfactant.

12. The method of claim 11, wherein the surfactant is selected from the group consisting of polysorbate 20, polysorbate 80, polyoxyethylene octyl phenyl ether, polyethylene glycol tert-octylphenyl ether, NP-40, polyoxyethylene lauryl ether, polyethylene glycol hexadecyl ether, octyl glucoside, octyl thioglucoside, n-dodecyl β-D-maltoside (DDM), 3-[(3-cholamidopropyl) dimethylammonio)-1-propanesulfonate (CHAPS), and 3-[(3-cholamidopropyl) dimethylammonio]-2-hydroxy-1-propanesulfonate (CHAPSO).

13. The method of claim 1, wherein the lysing of the bacteria is performed by sonication.

14. The method of claim 1, further comprising heating the lysate.

15. The method of claim 1, wherein the lysate is subjected to a method selected from the group consisting of affinity chromatography, size-exclusion chromatography, ion-exchange chromatography, hydrophobic interaction chromatography, and high-performance liquid chromatography (HPLC).

16. The method of claim 15, wherein the affinity chromatography is nickel (Ni)-affinity chromatography.

* * * * *